(12) United States Patent
Luo et al.

(10) Patent No.: US 7,656,146 B2
(45) Date of Patent: Feb. 2, 2010

(54) PARTICLE ANALYZER BASED ON SHEATH FLOW IMPEDANCE METHOD

(75) Inventors: Cheng Luo, Shenzhen (CN); Yan Yan, Shenzhen (CN); Jie Zhu, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 501 days.

(21) Appl. No.: 11/646,929

(22) Filed: Dec. 27, 2006

(65) Prior Publication Data
US 2008/0122423 A1    May 29, 2008

(51) Int. Cl.
*G01N 27/00* (2006.01)
*G01N 15/00* (2006.01)
*G01R 27/08* (2006.01)

(52) U.S. Cl. .................. 324/71.4; 324/691; 73/865.5
(58) Field of Classification Search ............... 324/71.4, 324/691
See application file for complete search history.

(56) References Cited

U.S. PATENT DOCUMENTS

| | | | |
|---|---|---|---|
| 3,793,587 A | 2/1974 | Thom et al. | |
| 3,810,010 A | 5/1974 | Thom | |
| 4,070,617 A | 1/1978 | Kachel et al. | |
| 4,165,484 A | 8/1979 | Haynes | |
| 4,198,160 A | 4/1980 | Kachel et al. | |
| 5,905,214 A | 5/1999 | Inami | |
| 6,259,242 B1 * | 7/2001 | Graham et al. | 324/71.4 |
| 6,417,658 B1 * | 7/2002 | Inami | 324/71.4 |
| 6,418,802 B1 * | 7/2002 | Wood | 73/865.5 |
| 6,515,492 B1 * | 2/2003 | Wood | 324/702 |
| 6,909,269 B2 * | 6/2005 | Nagai et al. | 324/71.4 |

\* cited by examiner

*Primary Examiner*—Jeff Natalini
(74) *Attorney, Agent, or Firm*—Vista IP Law Group, LLP.

(57) ABSTRACT

The application provides a particle analyzer based on sheath flow impedance method comprising a flow cell and a counting circuit, wherein the flow cell includes a front chamber and a back chamber, the front chamber includes a particle suspension liquid inlet and a front sheath liquid inlet, the back chamber includes a back sheath liquid inlet and a waste liquid outlet, an aperture being provided between the front and back chambers and each of the front and back chambers being connected to the counting circuit via an electrode respectively. The particle analyzer further comprise a back sheath liquid isolating chamber, the back sheath liquid stored on the bottom of the back sheath liquid isolating chamber flowing into the back chamber automatically and continuously due to the liquid level difference between the liquid in the back sheath liquid isolating chamber and the liquid in the back chamber, or due to a combination of said liquid level difference and the interior negative pressure of the back chamber. The particle analyzer may further comprise a waste liquid isolating chamber, which causes isolation of the internal fluid passageway connecting the inlet and the outlet of the waste liquid isolating chamber by the interior air. Back-flow of the liquid specimen can be prevented during a detection process, noises can be mitigated effectively, the sensitivity for detection of particles can be improved, and introduction of electromagnetic noises to the flow cell from the back sheath liquid or the waste liquid can be avoided.

20 Claims, 6 Drawing Sheets

PARTICLE ANALYZER BASED ON SHEATH FLOW IMPEDANCE METHOD

RELATED APPLICATION DATA

This application claims the priority of Chinese Patent Application No. 200610159876.6, filed on Nov. 2, 2006, the entire disclosure of which is expressly incorporated by reference herein.

FIELD

The application relates generally to a particle analyzer, and more particularly to a particle analyzer based on sheath flow impedance method to detect and analyze the number or the volume of particles by using the impedance of a sheath flow, and other applications thereof.

BACKGROUND

Techniques for detecting the number or the volume of particles by using the impedance of a sheath flow (known as "sheath flow impedance method") may be dated back to U.S. Pat. No. 3,793,587 and No. 3,810,010 in 1974. These patents involve some common elements, such as a flow cell including a front chamber and a back chamber, an aperture (or a small through hole), a sample tube, electrodes and a detection circuit. Here, the front and back chambers are connected via the aperture, with which the specimen tube is disposed coaxially. The outlet of the specimen tube is located at a position in the front chamber near the aperture, so as to introduce the particle suspension liquid to be detected (referred to as liquid specimen hereafter) into the flow cell. Each of the front and back chambers has a conductive particle free liquid source, hereafter referred to as front sheath flow and back sheath flow, respectively. The pressure of the front sheath flow is equal to the pressure of the liquid specimen at the outlet of the specimen tube; while the pressure of the back sheath flow may be much lower than the pressures of the former two.

In the counting circuit based on the sheath flow impedance, an electrode connected to the high-potential has to be placed in one of the front and back chambers, which is abbreviated as high-potential chamber; and a zero-potential electrode is placed in the other chamber, which is abbreviated as zero-potential chamber. To pass all the currents from the high-potential to the zero-potential through the aperture of the flow cell and ensure that interference will not be introduced or the sensitivity of the sensor will not be reduced due to the existence of other branch currents, it is preferable to isolate the high-potential chamber from the upstream of all liquid passages that supply conductive liquid to it, so as to avoid the possibility that branch currents are formed by connecting the upstream of these liquids to the zero-potential.

In U.S. Pat. No. 4,070,617 and No. 4,198,160, sheath liquid driving is implemented in the manner of driving by the liquid level difference. In U.S. Pat. No. 4,165,484, an exterior pressure source is introduced, in which a common air supply drives the sheath liquid in the storing chamber, and the liquid in the sheath liquid storing chamber is driven under the pressure to provide sheath liquid to the flow cell. To reduce the interference brought from the liquid storing chamber to the counting circuit, the inventors of U.S. Pat. No. 4,165,484 proposes a method of serially connecting a glass capillary tube within the sheath liquid supply passage, so as to increase the resistance of the liquid passage, and thus to achieve an effect of electromagnetic isolation. In this way, however, the liquid passage from the sheath liquid storing chamber to the flow cell plays a role of a conductive line unavoidably, thus introducing electromagnetic interfering signals into the flow cell. The signals will be superimposed on the impedance signals of the aperture, which makes it harder to identify signals. To decrease interferences, the glass capillary tube should be long and slim, which increases the operational risks. Meanwhile, to decrease interferences and avoid introducing additional electromagnetic interferences, electromagnetic valve, which is smaller and easily controllable, should be avoided to control the liquid passage. Furthermore, the driving pressure of the back sheath flow is larger in this method, thus causing increased consumption of liquid.

In U.S. Pat. No. 5,905,214, a positive pressure is applied and the driving force for ejecting the back sheath liquid into the back chamber is the positive pressure from the upstream chamber. To ensure that the positive pressure can be transmitted to the back chamber, the liquid passage along the way has to be sealed very nicely and a continuous liquid supply is a must. Consequently, it would be difficult to prevent exterior exoteric interfering signals from entering into the back chamber. In U.S. Pat. No. 6,909,269, the flow cell is placed within a special shielding box, which may attain shielding effect to some extent but cannot prevent occurrence of back-flow of the liquid specimen and generation of fake signals after the liquid specimen enters into the back chamber.

SUMMARY

To overcome the drawbacks in prior arts, one object is to provide a particle analyzer based on sheath flow impedance method, which enables fast detection of particles while mitigating signal noises effectively, improving the sensitivity for detection of particles and avoiding the introduction of electromagnetic noises into the flow cell from the back sheath flow or the waste liquid.

Another object is to ensure that the back sheath liquid can only flow from the outside to the inside of the back chamber during a particle detection process, thus to prevent the liquid specimen from back-flowing and contacting the wall of the chamber, and to keep the back chamber clean and to avoid pollution.

To fulfill the above objects, a particle analyzer based on sheath flow impedance method is provided, the particle analyzer comprising a flow cell and a counting circuit, wherein the flow cell includes a front chamber and a back chamber, the front chamber includes a particle suspension liquid inlet and a front sheath liquid inlet, the back chamber includes a back sheath liquid inlet and a waste liquid outlet, an aperture being provided between the front and back chambers so as to form a fluid passage between the front and back chambers, each of the front and back chambers being connected to the counting circuit via an electrode respectively, the particle analyzer further comprising a back sheath liquid isolating chamber, whose upper end communicates with the atmosphere on one hand and is connected to a sheath liquid storing chamber (i.e., sheath liquid supply source) through a pipeline on the other hand, and whose lower end is connected to the back chamber through a pipeline, back sheath liquid being stored on the bottom of the back sheath liquid isolating chamber. During a non-detection period, the back sheath liquid is supplied to the back sheath liquid isolating chamber from the sheath liquid storing chamber; during a detection period, the liquid passage for supplying liquid to the back sheath liquid isolating chamber is cut off, supply of the back sheath liquid from the sheath liquid storing chamber to the back sheath liquid isolating chamber is terminated, and the back sheath liquid in the back sheath liquid isolating chamber flows to the back chamber, with a result that air enters into the back sheath liquid isolating chamber via an interface on its top to form isolation air, causing air isolation of the internal fluid passage connecting the inlet and the outlet of the back sheath liquid isolating chamber; and during the detection period, the level of the back sheath liquid in the back sheath liquid isolating chamber is always maintained higher than the level of the back chamber.

Preferably, two interfaces are provided on the top of the back sheath liquid isolating chamber, one interface is connected to a one-way valve which only allows flow of liquid from the inside to of the chamber to the outside of the chamber, and the other interface is connected to a pipeline having two branches, one being connected to a sheath liquid supply source, and the other one being connected to another one-way valve which only allows flow of liquid from the outside of the chamber to the inside of the chamber and is located at the uppermost position for all liquid passages.

In this manner, during the detection process of the particle analyzer, the back sheath liquid flows towards the back chamber and air can enter into the back sheath liquid isolating chamber via an interface on its top, to form isolation air, thereby causing air isolation of the internal fluid passage connecting the inlet and the outlet of the back sheath liquid isolating chamber. While the air flows into the chamber, liquid in the pipeline through which it passes is pushed into the back sheath liquid isolating chamber to form an air column in the pipeline, to maintain and enhance the air isolation effect. In a period except the detection process, another branch at the upstream of the interface may supply liquid to the chamber and discharge the redundant air from the chamber through a one-way valve for another interface. The two one-way valves may implement their respective functions properly without additional control, and thus improve the system stability. Furthermore, during the detection process, the inside of the back sheath liquid isolating chamber is not subject to any liquid supply from outside, and the task of discharging back sheath liquid into the back chamber is performed only in the case of the standard atmospheric pressure and under the condition of being air isolated from the upstream supply source. At this time, the back sheath liquid flows into the back chamber due to the liquid level difference between the liquid in the back sheath liquid isolating chamber and the liquid in the back chamber, or due to a combination of said liquid level difference and the interior negative pressure of the back chamber. During a non-detection period, the back sheath liquid isolating chamber accepts and stores the supply of upstream back sheath liquid, for use in a subsequent detection process.

Preferably, the back sheath liquid isolating chamber is located at a position higher than the back chamber.

Preferably, the particle analyzer further comprises a waste liquid isolating chamber, which is located at a downstream position of the waste liquid outlet of the back chamber, wherein the top end of the waste liquid isolating chamber is connected to the waste liquid outlet and the bottom of the waste liquid isolating chamber is connected to a waste liquid chamber, the top end of the waste liquid isolating chamber also communicates with the atmosphere, causing air isolation of the internal fluid passage connecting the inlet and the outlet of the waste liquid isolating chamber.

Preferably, the waste liquid isolating chamber is located at a position lower than the back chamber, and the height of the pipeline connecting the waste liquid outlet and the waste liquid isolating chamber is lower than the highest liquid level of the back chamber.

Preferably, the particle analyzer further comprises a flow-limiting pipe serially connected within the pipeline between the back sheath liquid isolating chamber and the back chamber, to limit the velocity of the back sheath liquid flowing from the back sheath liquid isolating chamber to the back chamber, so as to decrease the usage amount of the back sheath liquid, to greatly reduce the capacity of the back sheath liquid isolating chamber as required and hence to reduce the volume of the back sheath liquid isolating chamber, so that it is easier and more feasible to store/supply the back sheath liquid in/from the back sheath liquid isolating chamber. Furthermore, the amount of the liquid ultimately flowing from the waste liquid outlet to the waste liquid isolating chamber can only form discontinuous liquid drops, instead of continuous liquid jet, so as to form air isolation between the liquid on the bottom and the liquid on the top of the waste liquid isolating chamber.

Preferably, a waste liquid buffering chamber is provided at an upstream position of the waste liquid isolating chamber, so that a larger amount of waste liquid generated during the counting operation is stored temporarily in the waste liquid buffering chamber and then discharged into the waste liquid isolating chamber. In this manner, isolation may be achieved when the waste liquid cannot be discharged to the waste liquid isolating chamber directly in form of liquid drops due to increase in the amount of the back sheath liquid.

Preferably, all liquid in the front chamber and in its two inlets is connected to a zero-potential electrode, and the back chamber is connected to a high-potential electrode, the current unable to return to a zero-potential through other passages (for example, the upstream of the back sheath liquid) except the aperture, thus making the aperture to be the only passage from the high-potential electrode to the zero-potential electrode, the zero-potential electrode and the high-potential electrode are connected to the counting circuit, respectively.

Preferably, the particle analyzer further comprises a grounded metal shielding box, within which the flow cell, the back sheath liquid isolating chamber and the waste liquid isolating chamber are placed.

Preferably, besides that the back sheath liquid and the waste liquid are isolated by the back sheath liquid isolating chamber and the waste liquid isolating chamber respectively and the pipeline connected to the atmosphere is air blocked, liquid in other pipelines connected to the flow cell, in the pipeline supplying liquid to the back sheath liquid isolating chamber and in the pipeline leading from the waste liquid isolating chamber to the waste liquid chamber is connected to the shielding box, that is, the potential is zero.

Preferably, the front sheath liquid inlet is connected via a pipeline to a sheath liquid storing chamber, which is connected with a positive pressure source, so that the positive pressure source supplies air to drive the front sheath liquid and thus the positive pressure source applies pressure to the sheath liquid storing chamber, to supply front sheath liquid directly to the flow cell, and hence to apply more pressure to the front sheath liquid. Meanwhile, the pressure of the back chamber is only formed by the liquid level difference between the liquid in the back sheath liquid isolating chamber and the liquid in the back chamber, or due to a combination of said liquid level difference and the interior negative pressure of the back chamber. Accordingly, the difference between the pressures in the front and back chambers is larger, thus the velocity of the liquid passing through the aperture is increased, so that a fast detection can be realized.

Preferably, the particle suspension liquid is introduced into the front chamber through a specimen tube and the waste liquid is discharged out of the back chamber through an outlet pipe.

Preferably, one end of the specimen tube outside the front chamber acts as the particle suspension liquid inlet, and one end of the outlet pipe outside the back chamber acts as the waste liquid outlet.

Preferably, the sheath liquid storing chamber stores particle free liquid for supply.

Preferably, the front sheath liquid and the back sheath liquid are conductive and contain no particle, thus forming a front sheath flow and a back sheath flow respectively during the detection period, and the particle suspension liquid containing particles to be detected forms a liquid specimen passing through the aperture.

Preferably, the front chamber, the back chamber and the aperture are all made of insulating materials.

Preferably, the aperture is provided on a cylindrical, artificial ruby sheet, and its inner diameter and depth are both less than 100 microns.

Preferably, during the detection period, the back sheath liquid in the back sheath liquid isolating chamber flows into the back chamber automatically and continuously due to the liquid level difference from the back chamber and/or the interior negative pressure of the back chamber.

Preferably, the bottom of the waste liquid buffering chamber is connected with the top of the waste liquid isolating chamber via a pipeline, the inner diameter of which is limited so that the waste liquid is gradually discharged from the waste liquid buffering chamber into the waste liquid isolating chamber in form of liquid drops.

Preferably, the bottom of the waste liquid buffering chamber is connected with the top of the waste liquid isolating chamber via a pipeline, on which a valve is provided so that the waste liquid is discharged from the waste liquid buffering chamber into the waste liquid isolating chamber under the control of the valve.

In comparison with prior arts, the particle analyzer based on sheath flow impedance method has the notable advantages as follows.

Liquid can be pre-injected into the back sheath liquid isolating chamber under the positive pressure, and during the detection and counting process, the injection is stopped, and the back sheath liquid is isolated from its upstream liquid supply by the air in the upper portion of the back sheath liquid isolating chamber, the back sheath liquid flows into the back chamber automatically and continuously due to gravity or due to a combination of gravity and the interior negative pressure of the back chamber, so as to form the back sheath flow. That is, during the detection process, the liquid passage for supplying liquid to the back sheath liquid isolating chamber will be cut off, and the liquid supply from the sheath liquid storing chamber to the back sheath liquid isolating chamber is terminated. This avoids the possibility of bringing external interfering signals during the detection process due to the fact that the supply liquid in the upper portion of the back sheath liquid isolating chamber is fluid communicated with the back sheath liquid in the lower portion and guarantees the effectiveness of air isolation. Furthermore, since the back sheath liquid isolating chamber and the waste liquid isolating chamber can isolate the liquid passage of the back chamber leading to the upstream of the back sheath liquid and the downstream of the waste liquid by internal air, and the air passing through the one-way valve can form air column isolation in the pipeline between the back sheath liquid isolating chamber and the sheath liquid storing chamber. This guarantees and increases the effectiveness of air isolation, so that all currents from the high-potential to the zero-potential pass through the aperture of the flow cell and interferences will not be caused or the sensitivity of the particle analyzer will not be reduced due to the existence of the other current branches. In this manner, branching effect by the back sheath liquid or the waste liquid to the current can be completely avoided, and noises brought from the back sheath liquid or the waste liquid can be isolated.

Additionally, since a back sheath liquid isolating chamber is employed, wherein during the detection and counting process, the level of the back sheath liquid in the back sheath liquid isolating chamber is always maintained higher than the level of the back chamber, the inventive particle analyzer may supply the back sheath liquid to the back chamber due to the liquid level difference between the liquid in the back sheath liquid isolating chamber and the liquid in the back chamber, or due to a combination of said liquid level difference and the interior negative pressure of the back chamber. This ensures that the liquid specimen will not contact the chamber wall due to back-flow during the particle detection process and the back chamber is kept clean and pollution is avoided.

Furthermore, since the front sheath liquid may be driven by the pressure of air source and the back sheath liquid may be driven under the action of the liquid level difference between the liquid in the back sheath liquid isolating chamber and the liquid in the back chamber or a combination of said liquid level difference and the interior negative pressure of the back chamber, a larger pressure difference is formed between the front and back chambers, and thus a larger amount of particles may be counted quickly.

In addition, since the flow cell, the back sheath liquid isolating chamber and the waste liquid isolating chamber can be placed within a shielding box, the possibility of bringing external interferences from the back sheath liquid or the waste liquid can be completely eliminated.

BRIEF DESCRIPTION OF THE DRAWINGS

The features and advantages will become apparent and be appreciated from the following descriptions with reference to exemplary embodiments when taken in conjunction with the accompanying drawings. The exemplary embodiments are intended to be only illustrative, rather than to limit the invention.

DETAILED DESCRIPTION

Figure 1:
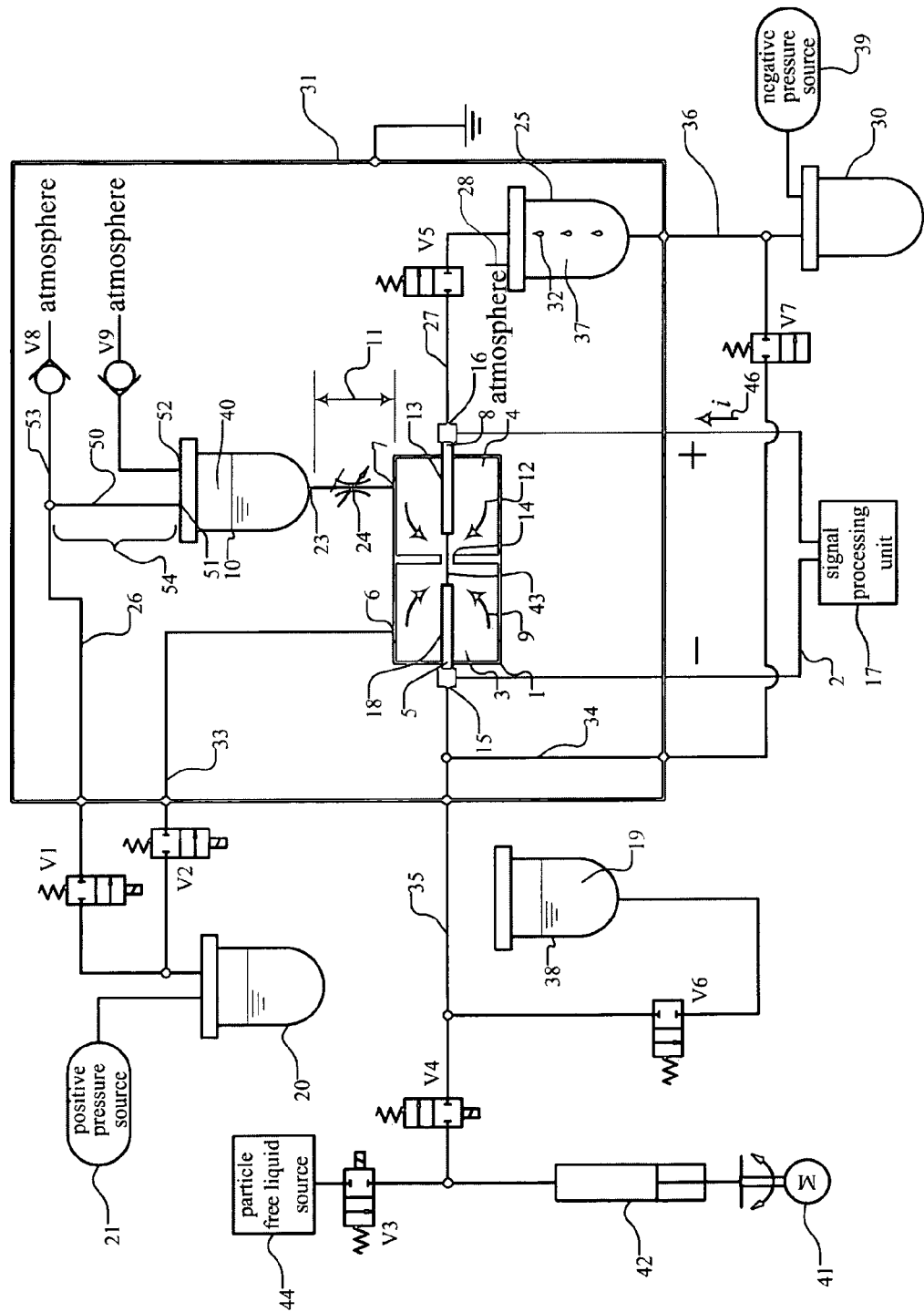
FIG. 1 is a schematic view illustrating the liquid passages and the signal detection circuit of a particle analyzer according to an embodiment.
Figure 3:
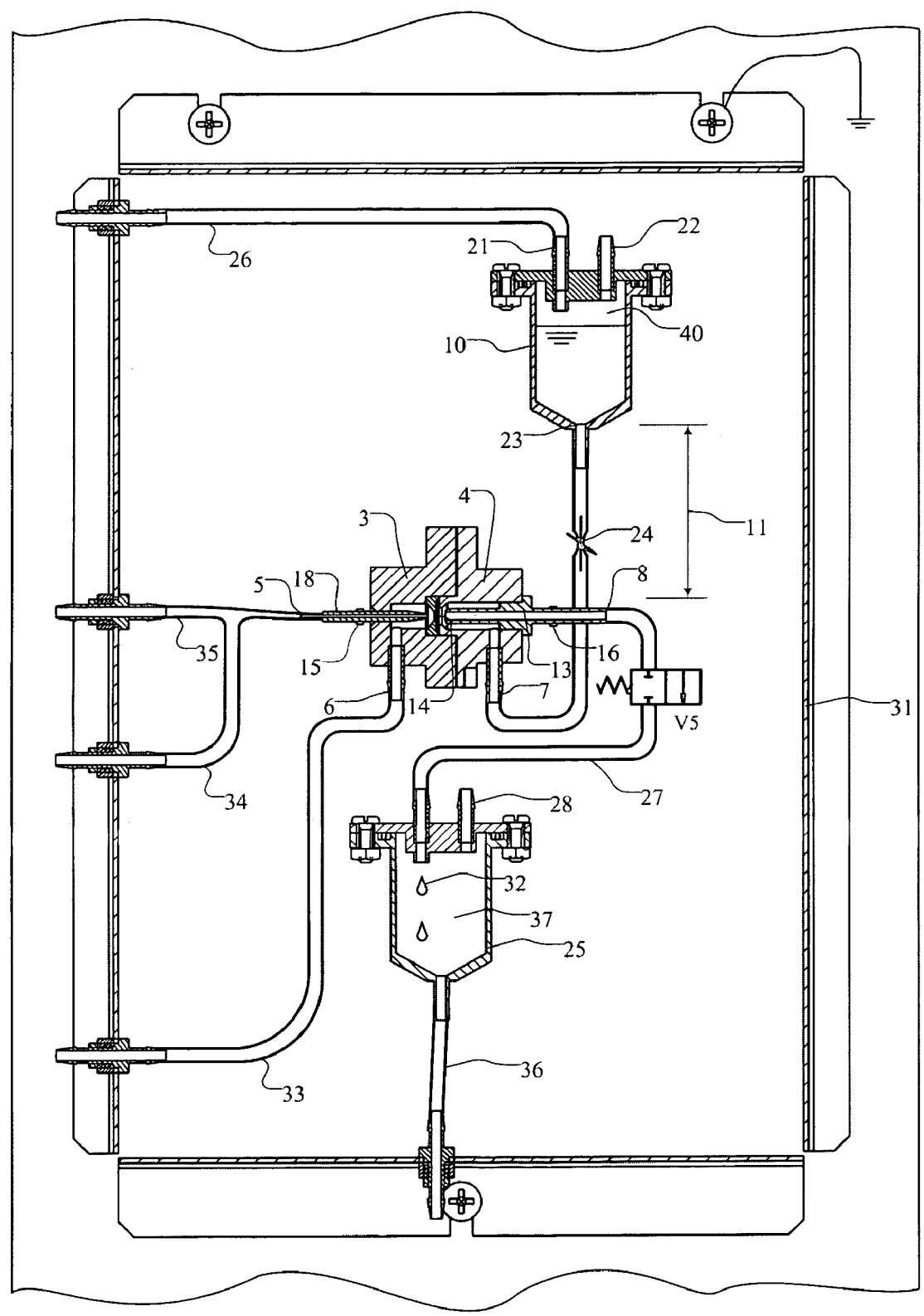
FIG. 3 is a sectional view showing a shielding box and its internal components.

As shown in FIG. 1 and FIG. 3, the particle analyzer based on sheath flow impedance method according to an exemplary embodiment comprises a flow cell 1 and a counting circuit 2. The flow cell 1 comprises a front chamber 3 and a back chamber 4, the front chamber 3 includes a particle suspension liquid inlet 5 (for example, served by one end of a specimen tube 18 outside the flow cell) and a front sheath liquid inlet 6, the back chamber 4 includes a back sheath liquid inlet 7 and a waste liquid outlet 8 (for example, served by one end of an outlet pipe 13 outside the flow cell). The front sheath liquid and the back sheath liquid are conductive and contain no particle, thus forming a front sheath flow 9 and a back sheath flow 12 respectively in the front and back chambers while in use. The specimen tube 18 and the outlet pipe 13 are made of conductive metal. A back sheath liquid isolating chamber 10 is provided at a position higher than the flow cell 1 (especially, the back chamber 4), to supply the back sheath flow 12 to the back chamber due to the liquid level difference 11 or due to a combination of the liquid level difference 11 and the interior negative pressure of the back chamber, and envelops the liquid flowing from the front chamber 3 to enter into the outlet pipe 13. A waste liquid isolating chamber 25 is located at the downstream of the flow cell, with its height (or, the horizontal position) lower than the highest internal liquid level of the flow cell 1 (especially, the back chamber 4), and its lower end being connected to a negative pressure source 39. An aperture 14 is provided between the front and back chambers to form the only liquid path between the front and back chambers. The counting circuit 2 has two electrodes, where all the liquid in the front chamber and in its two inlets is connected to a zero-potential electrode 15, and the liquid in the back chamber is connected to a high-potential electrode 16. The front chamber 3, the back chamber 4 and the aperture 14 are all made of insulating materials. The portion of the back sheath liquid isolating chamber 10 connected to a pipeline 50 is insulated from its portion connected to an interface 23, and the portion of the waste liquid isolating chamber 25 connected to a pipeline 27 is insulated from its portion connected to a pipeline 36. Therefore, the current is unable to return to a zero-potential through other non-fluid media (such as the chamber body) except the aperture. Meanwhile, the internal liquid passage connecting the top interface and the bottom outlet of the back sheath liquid isolating chamber 10 is isolated by insulating air, and it is also true for the waste liquid isolating chamber 25 (to be detailed hereafter). In this manner, the aperture 14 becomes the only liquid passage from the high-potential electrode to the zero-potential electrode, and the two electrodes are both connected to a signal processing unit 17.

The interior for each of the front and back chambers 3 and 4 is cylindrical (alternatively, other shapes are also possible as required), with its axis coplanar with the horizontal plane and collinear with the axis of the aperture 14, the axis of the specimen tube 18 and the outlet pipe 13. The aperture 14 is provided on a cylindrical, artificial ruby sheet, and its inner diameter and depth are both less than 100 microns. The ruby sheet is mounted between the front and back chambers. The specimen tube 18 has a through-hole along the axial direction, to provide a path for injecting the particle suspension liquid 19 into the flow cell.

There are two inlets leading to the interior of the front chamber 3, one of which is the specimen tube 18 and the other one is the front sheath liquid inlet 6. The front sheath liquid inlet 6 is connected to a sheath liquid storing chamber 20. A positive pressure source 21 supplies pressure to the sheath liquid storing chamber 20, thus providing a front sheath flow 9 to the flow cell 1.

The interior body of the back sheath liquid isolating chamber 10 is formed in shape of a closed cavity having a cylindrical upper portion and a substantially conical lower portion and has an axis extending along the vertical direction. Two interfaces 51 and 52 are provided on the top of the back sheath liquid isolating chamber 10. The interface 52 is connected to a one-way valve V9, which allows flow of liquid from the inside of the back sheath liquid isolating chamber to the outside of the back sheath liquid isolating chamber, and stops flow in the reverse direction. The interface 51 is connected to a pipeline 50 having two branches 26 and 53. The pipeline branch 26 may reach the sheath liquid storing chamber 20, and the pipeline branch 53 is connected to another one-way valve V8. The valve V8 is installed in an opposite fashion, which only allows flow of liquid from the outside of the back sheath liquid isolating chamber to the inside of the back sheath liquid isolating chamber and stops flow in the reverse direction. Further, the one-way valve V8 is located at the uppermost position for all liquid passages. Back sheath liquid is stored on the bottom of the back sheath liquid isolating chamber 10. During a detection process, air can enter into the back sheath liquid isolating chamber 10 through the pipelines 53 and 50 from the one-way valve V8. While the air flows into the back sheath liquid isolating chamber, the liquid in the pipelines 53 and 50 is pushed into the back sheath liquid isolating chamber 10, to form an air column 54 in this pipeline, so as to guarantee and increase the effectiveness of air isolation during the subsequent detection process, and isolation air 40 is formed in the upper space of the back sheath liquid isolating chamber. In a period other than the detection process, the other branch 26 at the upstream of the interface 51 can supply liquid to the back sheath liquid isolating chamber and discharge the redundant air in the back sheath liquid isolating chamber from the one-way valve V9.

The two one-way valves V8 and V9 can implement their own functions without additional control and thus the system stability is enhanced.

During the detection process, the interior of the back sheath liquid isolating chamber 10 is subject to no exoteric liquid supply. The task of injecting back sheath liquid into the back chamber 4 is only performed in the case of the standard atmospheric pressure and under the condition of being air isolated from the liquid in the upstream sheath liquid storing chamber 20. At this time, the back sheath liquid flows into the back chamber 4 automatically and continuously due to the liquid level difference between the liquid in the back sheath liquid isolating chamber 10 and the liquid in the back chamber 4, or due to a combination of said liquid level difference and the interior negative pressure of the back chamber 4. During a non-detection period, the back sheath liquid isolating chamber receives and stores the upstream supply of back sheath liquid, for use in later detection. The bottom 23 of the back sheath liquid isolating chamber is connected to the back chamber 4 of the flow cell, and is located at a position higher than the back chamber 4. During a counting process, the level of the back sheath liquid isolating chamber is always maintained higher than the level of the back chamber 4.

A flow-limiting pipe 24 is located within the pipeline connecting the back sheath liquid isolating chamber 10 and the back chamber 4, to limit the velocity of the back sheath liquid flowing from the back sheath liquid isolating chamber 10 to the back chamber 4 so as to decrease the usage amount of the back sheath liquid, to greatly reduce the capacity of the back sheath liquid isolating chamber 10 and hence to reduce the volume of the back sheath liquid isolating chamber 10, so that it is easier and more feasible to store/supply the back sheath liquid in/from the back sheath liquid isolating chamber 10. Furthermore, the amount of the liquid flowing from the outlet pipe 13 to the waste liquid isolating chamber 25 is controlled, to only form discontinuous liquid drops, instead of continuous liquid jet, so that the air 37 isolates the liquid on the bottom and the liquid on the top of the waste liquid isolating chamber 25.

The back sheath flow 12 is injected into the back chamber 4 of the flow cell from the back sheath liquid isolating chamber 10 through the flow-limiting pipe 24. Liquid is supplied from the sheath liquid storing chamber 20 to the back sheath liquid isolating chamber 10 through the pipelines 26 and 50.

The outlet pipe 13 is the only exit of the flow cell. One end of the outlet pipe 13 outside the flow cell 1 is connected to the waste liquid isolating chamber 25 through a pipeline 27. The horizontal positions (or the heights) of the pipeline 27 and the waste liquid isolating chamber 25 are both below the uppermost internal level of the flow cell 1. The waste liquid isolating chamber 25 has a structure similar to the back sheath liquid isolating chamber 10, in which an inlet on the top is connected to the outlet pipe 13, an air inlet/outlet 28 is open to the air, and an outlet on the bottom is connected to a waste liquid chamber 30 with a negative pressure. Thus, there is no liquid accumulation in the waste liquid isolating chamber 25.

Figure 7A:
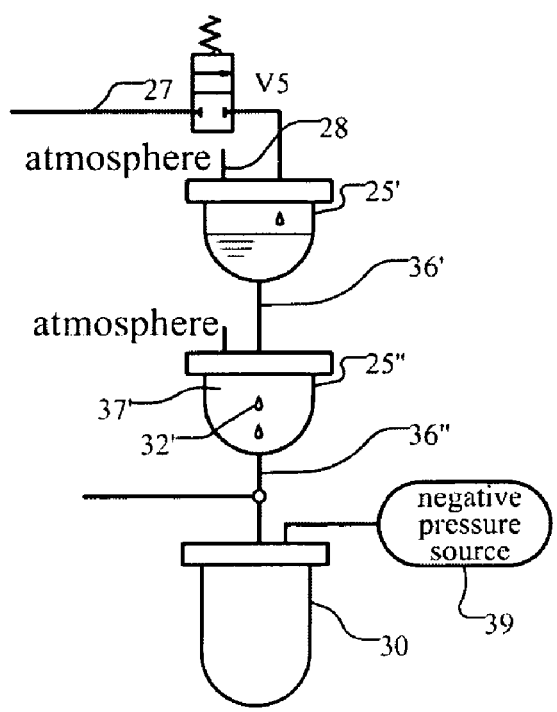
FIGS. 7a and 7b are schematic views illustrating two variant embodiments of the waste liquid isolating chamber, respectively.
Figure 7B:
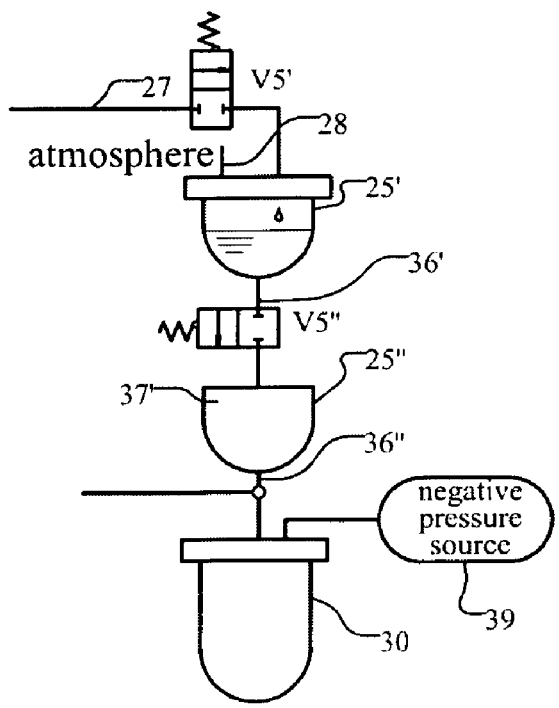

In addition to the embodiment described above, the isolation effect of the inventive waste liquid isolating chamber can be obtained by other embodiments as shown in FIGS. 7a and 7b.

Specifically, as shown in FIGS. 7a and 7b, a waste liquid buffering chamber 251 is provided at an upstream position of the waste liquid isolating chamber 25. The top of the waste liquid buffering chamber 251 is open to the air via an air inlet/outlet 28 and connected to a valve V5 via a pipeline, and the bottom of the waste liquid buffering chamber 251 is connected with the top of the waste liquid isolating chamber 25 via a pipeline 361. The portion of the waste liquid isolating chamber 25 being connected to the pipeline 361 is insulated from its portion being connected to a pipeline 362. In this manner, a larger amount of waste liquid generated during a counting operation may be stored temporarily in the waste liquid buffering chamber 251 and redundant air is then discharged through the air inlet/outlet 28. The waste liquid buffering chamber 251 can be emptied by means of limiting or reducing the inner diameter of the pipe 361 so that the waste liquid is released gradually in form of liquid drops 321 to the waste liquid isolating chamber 25 under the action of gravity. At this time, isolation air 371 always exists in the upper portion of the waste liquid isolating chamber 25, as shown in FIG. 7a. Alternatively, a valve V51 can be added to the pipeline 361 and the interface for connecting the upper portion of the waste liquid isolating chamber 25 to the air can be omitted. In this way, the valve V51 is closed during a detecting and counting period so that a larger amount of waste liquid generated during the counting operation can be stored temporarily in the waste liquid buffering chamber 251 and the redundant air is discharged through the air inlet/outlet 28. The air 371 in the waste liquid isolating chamber 25 isolates the waste liquid at the upstream from that at the downstream. During a non-counting period, the valve V51 is opened so that the waste liquid in the waste liquid buffering chamber 251 is injected into the waste liquid isolating chamber 25 under the action of gravity. Air will be supplied through the air inlet/outlet 28 on the top of the waste liquid buffering chamber 251, and enter into the waste liquid isolating chamber 25 through the pipeline 361 after the waste liquid buffering chamber 251 is emptied. The isolation air 371 is thus formed, and at this time, the waste liquid need not be emptied in form of liquid drops, as shown in FIG. 7b.

When the flow rate of the back sheath flow is increased so that the waste liquid cannot be released directly in form of liquid drops into the waste liquid isolating chamber, the above two alternative embodiments can be used to obtain the isolation effect.

Figure 2:
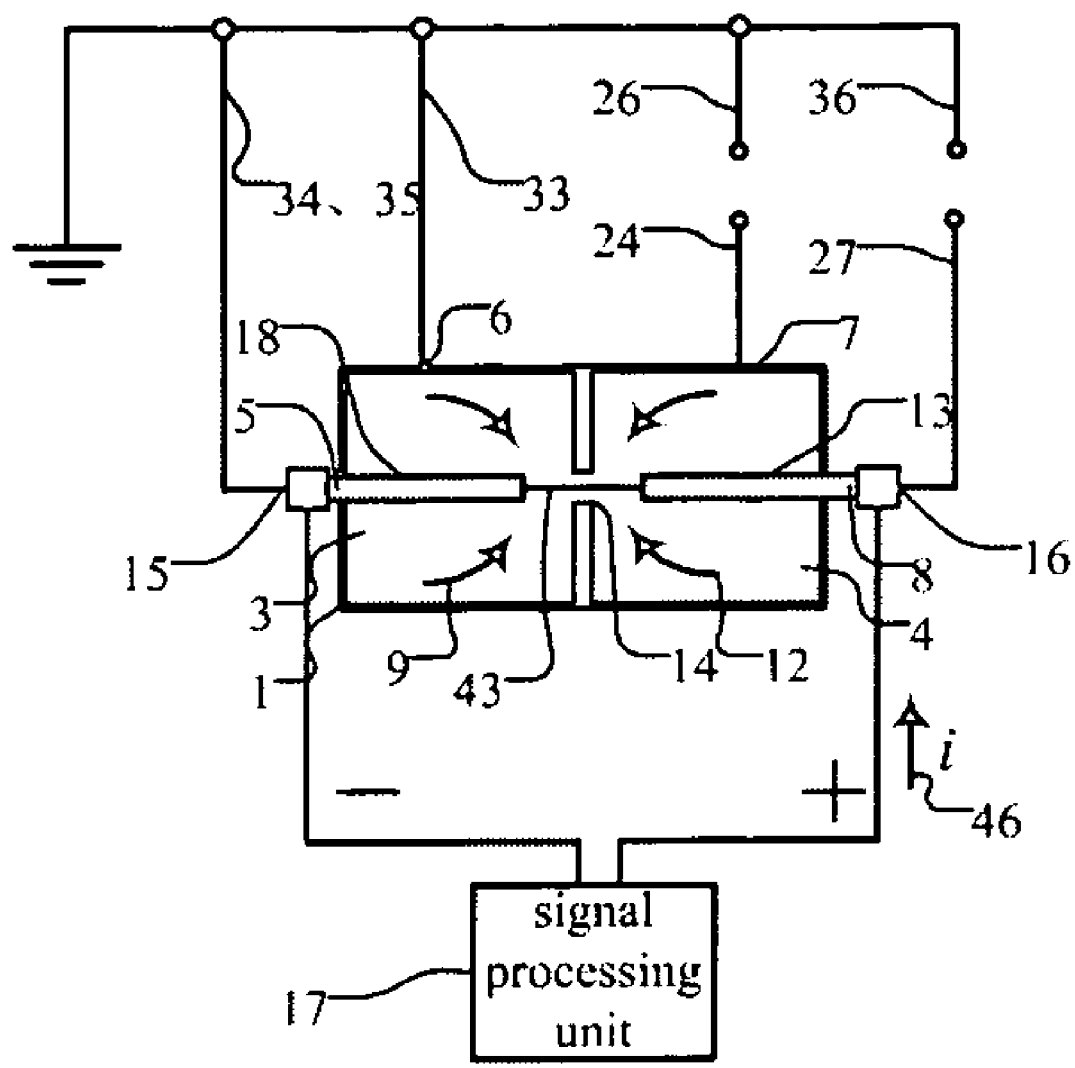
FIG. 2 is a schematic view illustrating a circuit equivalent to that of FIG. 1.
Figure 4:
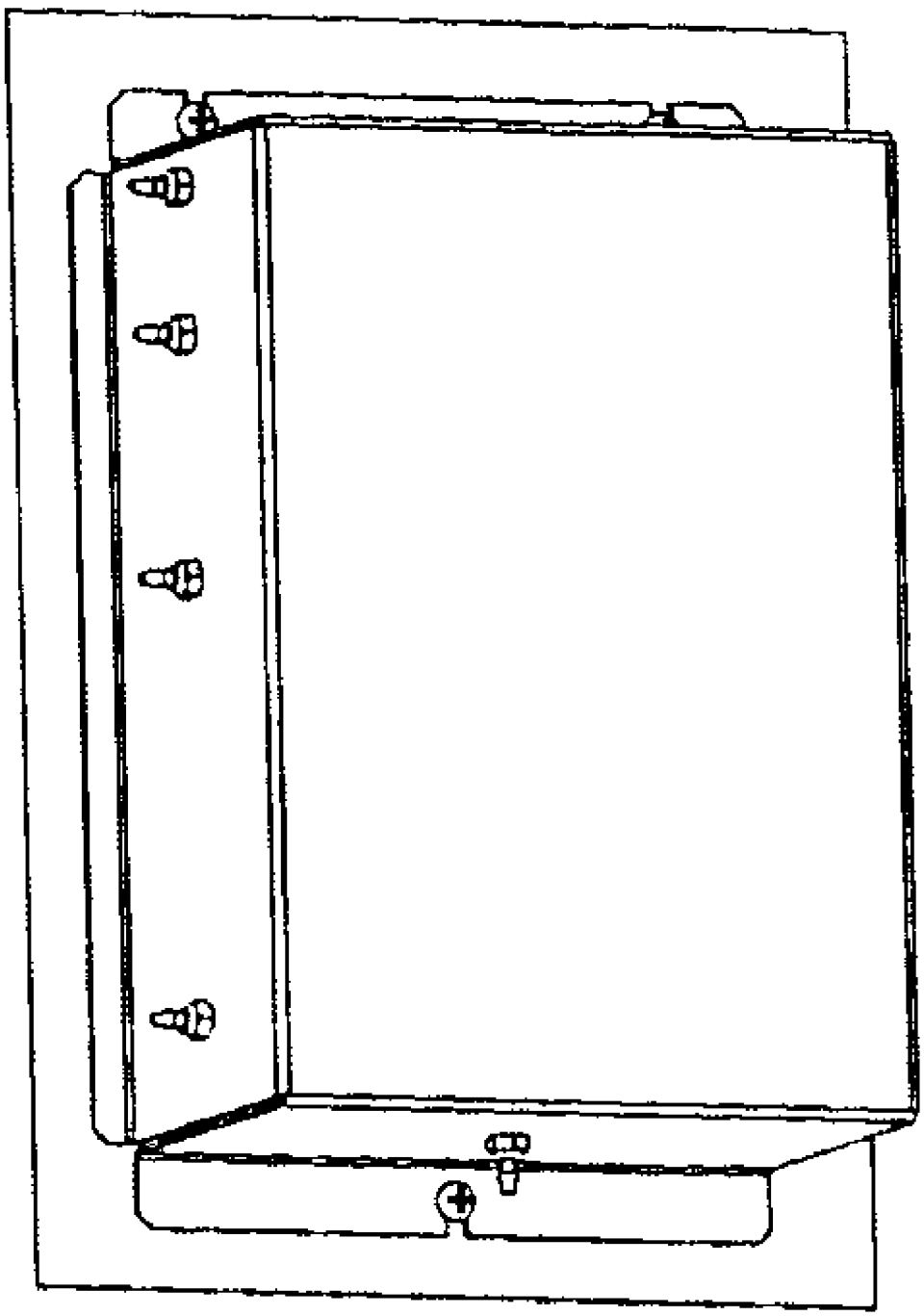
FIG. 4 shows the appearance of the shielding box.

As shown in FIG. 4, a shielding box 31 is a grounded metal box, within which the flow cell 1, the back sheath liquid isolating chamber 10 and the waste liquid isolating chamber 25 are placed. As shown in FIG. 2, besides that the back sheath flow 12 and the waste liquid 32 are isolated respectively by the back sheath liquid isolating chamber 10 and the waste liquid isolating chamber 25 and the pipeline connected to the atmosphere is air blocked (that is, the current is cut off), liquid in other pipelines 33, 34 and 35 connected to the flow cell 1, in a pipeline 26 supplying liquid to the back sheath liquid isolating chamber 10, and in a pipeline 36 leading from the waste liquid isolating chamber 25 to the waste liquid chamber 30 is connected to the shielding box 31, that is, the potential is zero.

The signal processing unit 17 provides driving signals to the impedance-based sensor composed of the flow cell 1, and converts a weak original signal into a signal satisfying the A/D input requirements for later algorithm identification and counting. The signal arises from the change of the resistance characteristic between the two ends of the aperture when particles in the liquid specimen pass through the aperture. Two electrodes 15 and 16 are provided in the flow cell and are connected to the signal processing unit 17, wherein the high-potential electrode 16 is connected to the back chamber and the zero-potential electrode 15 is connected to the front chamber.

The inventive particle analyzer based on sheath flow impedance method will perform a counting process in implementing detection as follows.

First, a suspension liquid containing the particle to be detected is diluted in accordance with a predetermined dilution ratio (for example, 1:1000) to obtain the liquid specimen, which is injected into a pre-mixing chamber 38. Valves V6 and V7 are then opened. Due to the action of the negative pressure source 39 on the waste liquid chamber, the liquid specimen is sucked under the negative pressure of the waste liquid chamber 30 to fill the pipeline 35. Then, valves V6 and V7 are closed and valve V1 is opened, and the positive pressure source 21 supplies liquid to the back sheath liquid isolating chamber 10 from the sheath liquid storing chamber 20. The one-way valve V8 stops the liquid from entering into the branch 53 automatically. Meanwhile, the air in the upper portion of the back sheath liquid isolating chamber 10 is released through the interface 52 and the valve V9 upon the liquid injection. The valve V1 is closed before the level of the back sheath liquid isolating chamber 10 reaches the top of the chamber and then the valve V5 is opened. The liquid in the back sheath liquid isolating chamber 10 may flow towards the flow cell 1 through the flow-limiting pipe 24 and bring the air flow from the valve V8 to the back sheath liquid isolating chamber along the pipelines 53 and 50. Thus, the liquid in the pipeline is pushed into the back sheath liquid isolating chamber and an air column 54 is formed in the pipeline 50, so that the air 40 in the pipeline 26 or the air column 54 in the pipelines 53 and 50 isolates the back sheath liquid isolating chamber 10 from the back sheath liquid supply pipeline 26.

At this time, the back sheath flow 12 has been formed and then the valve V2 is opened, to bring sheath liquid and positive pressure from the sheath liquid storing chamber 20 to the front chamber 3 so that the liquid in the front chamber 3 flows through the aperture 14 into the back chamber 4 to form a front sheath flow 9.

Then the valve V4 is opened and a motor 41 is controlled to push an injector 42 so that the liquid specimen in the pipeline 35 is pushed into the flow cell 1 through the specimen tube 18. The liquid specimen begins to converge at the outlet of the specimen tube 18 under the action of the front sheath flow 9, becoming slimmer and faster gradually, flows along the axial direction of the aperture 14 and is enveloped by the front sheath flow 9 to pass through the center of the aperture 14. When passing through the aperture 14, a liquid jet 43 is formed with a very high velocity and a diameter less than that of the aperture 14. The diameter of the liquid jet 43 can be adjusted to be equal to the diameter of a particle to be detected by adjusting the speed of the motor 41 driving the injector, to avoid the possibility that multiple particles pass through the aperture simultaneously.

Since the particles to be detected (for example, blood cells) are poor conductors, they will replace the conducting liquid when the liquid specimen 43 containing particles to be detected passes through the aperture 14, leading to a change in the impedance characteristics of the aperture. Because the aperture 14 is the only path from the high-potential electrode to the zero-potential electrode, the impedance characteristics between electrodes 15 and 16 will change accordingly. The change is proportional to the volume of the particles. The signal processing unit 17 converts the change into a pulse waveform and the volume distribution of the particles and the number of the particles can be obtained by analyzing the size and the number of the pulse waveform.

Being enveloped by the front sheath flow 9, the liquid specimen 43 passes through the aperture 14 and then enters into the back chamber 4. The two continue to flow along the axial direction while being enveloped by the back sheath flow 9 formed already and enter into the outlet pipe 13. The liquid that has entered into the outlet pipe 13 finally flows into the waste liquid isolating chamber 25 along the pipeline 27.

Under the adjustment of the flow-limiting pipe 24, the amount of the liquid flowing into the waste liquid isolating chamber 25 from the outlet pipe 13 can only form discontinuous liquid drops 32, instead of continuous liquid jet, so as to isolate the liquid on the bottom from the liquid on the top of the waste liquid isolating chamber 25 by air 37. The liquid 32 that has entered into the waste liquid isolating chamber 25 reaches the bottom of the waste liquid isolating chamber 25 under the action of gravity and flows into the waste liquid chamber 30 under the action of the negative pressure source 39.

After the counting operation is completed, the back sheath flow 12 keeps on being injected into the back chamber, the motor 41 stops pushing the injector 42 and injecting the liquid specimen into the flow cell 1. Next, the valve V2 is closed to stop supply of the front sheath flow 9 to the front chamber 3. In the last, the valve V5 is closed to stop supply of the back sheath flow 12 to the flow cell 1. Then, a cleaning procedure is performed, to clean the flow cell 1 and the components connected therewith.

Hereafter, the valve V4 is closed and the valve V3 is opened, and the motor 41 driving the injector rotates in a reverse direction, so that the injector 42 sucks full-scale liquid from the particle free liquid source 44.

The counting process comes to an end so far.

It has been found that to accomplish counting based on the sheath flow impedance, the pressure at the inlet of the specimen tube 18 should be slightly larger than the pressure at the front sheath liquid inlet 6 so that the liquid specimen passes through the aperture 14 along the axial direction while being enveloped by the front sheath flow 9 and pulse waveforms with good repeatability and nice legibility are obtained. Meanwhile, to guarantee that no turnaround will occur after the particles contained in the liquid specimen pass through the aperture and hence duplicate signals will not be generated and that the front and back chamber walls are kept clean from being polluted by the liquid specimen, a back sheath flow 12 is added into the front chamber 4. The pressure at the back sheath liquid inlet 7 is less than the pressure at the front sheath liquid inlet 6, and the back sheath flow 12 envelops the front sheath flow 9 and the liquid specimen 43 to enter into the outlet pipe 13.

Figure 5:
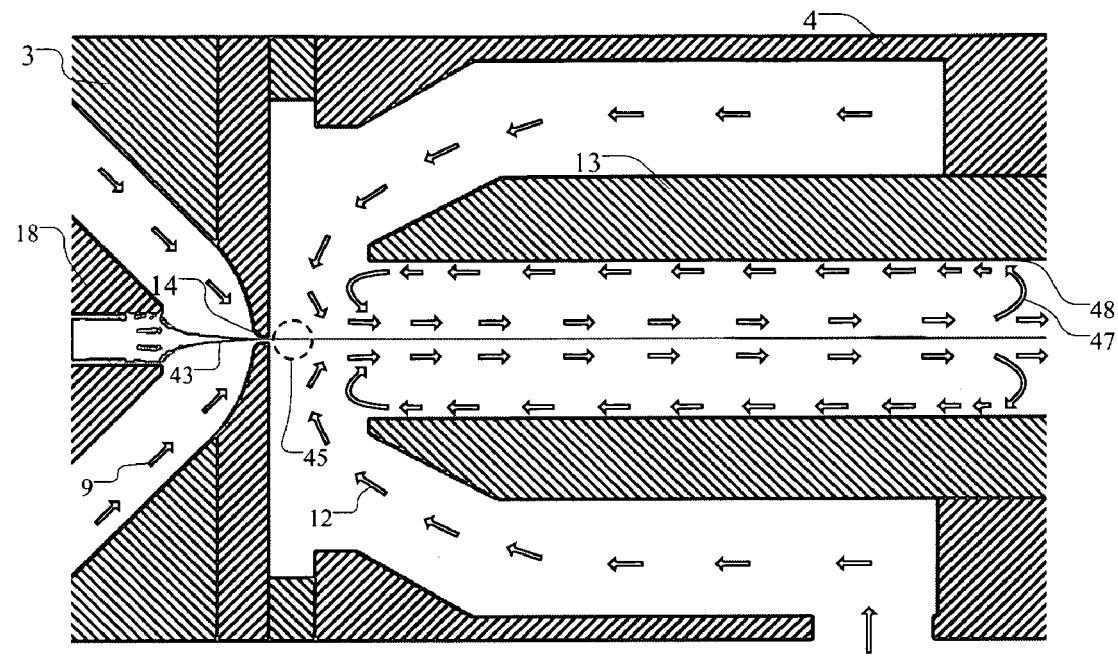
FIG. 5 is a schematic view showing a case where the liquid specimen back-flows in the outlet pipe when the back sheath flow is only driven under the negative pressure generated in the liquid jet surrounding area near the aperture in the back chamber.
Figure 6:
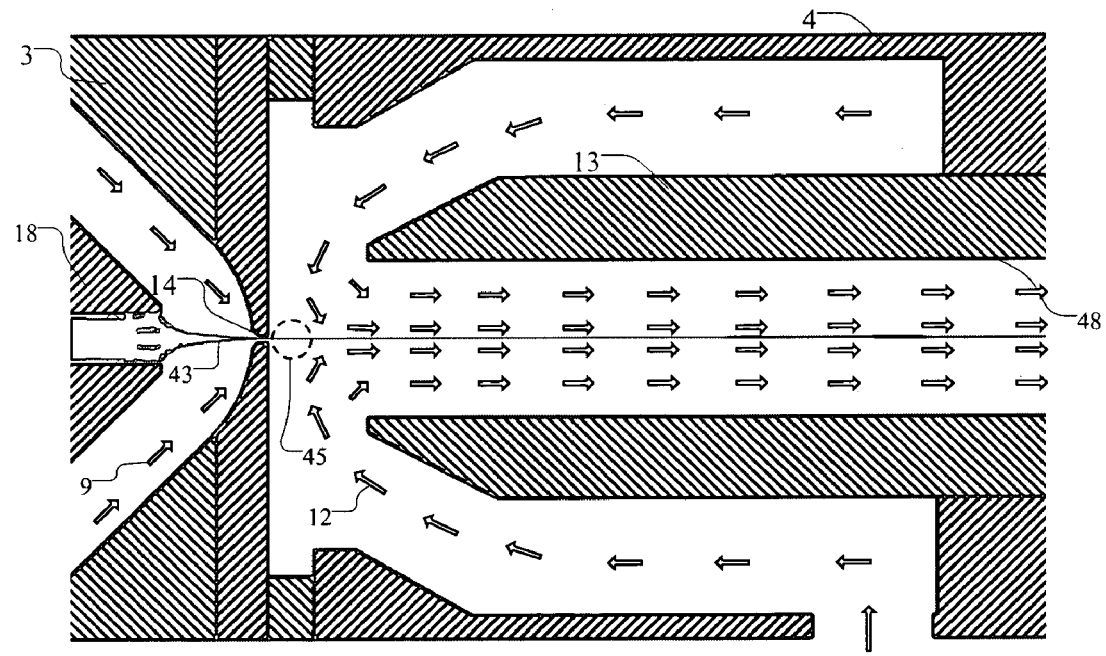
FIG. 6 is a schematic view showing a case where the back sheath flow is driven under both the negative pressure generated in the liquid jet surrounding area near the aperture in the back chamber and the liquid level difference.

It's further desired to pass more particles within a short period of time. For this purpose, a larger pressure is applied to the front sheath flow 9 by increasing and using an external positive pressure source (or, positive pressure source 21) to obtain a larger pressure difference between the front and back chambers so that the velocity for the liquid to pass through the aperture 14 becomes faster. In this manner, the number of particles detected per second can reach up to 10 k or more, for example. It has been proven through simulation and test that there is no need to increase the pressure of the back sheath flow 12 while the pressure of the front sheath flow 9 is increased. In fact, a larger pressure difference between the front and back chambers will lead to a higher velocity of flow for the front chamber liquid to pass through the aperture 14, and a liquid jet coaxial with the aperture 14 is formed. Near the aperture 14 in the back chamber, as shown in FIGS. 5 and 6, the liquid jet surrounding area 45 will produce a negative pressure lower than the standard atmospheric pressure. The larger the pressure difference is, the larger the negative pressure will be generated in the back chamber 4. The back sheath flow 12 may enter into the back chamber 4 automatically under the action of the difference between the pressure and the atmosphere, thus implementing functions of enveloping the liquid specimen 43 and the front sheath flow 9 and prevention of back-flow or polluting the back chamber. For this reason, a back sheath liquid isolating chamber 10 is presented, whose upper end communicates with (or is open to) the atmosphere and whose lower end is connected to the back chamber 4. While in counting, the internal liquid level of the back sheath liquid isolating chamber is always maintained higher than the liquid level of the back chamber, and thus the external driving of the back sheath flow 12 can y be achieved.

Meanwhile, the back sheath liquid isolating chamber 10 and waste liquid isolating chamber 25 isolates the fluid passages from the back chamber 4 to the upstream of the back sheath liquid and the downstream of the waste liquid by the internal air or the air column 54 in the pipeline 50. Thus, the branching effect of the back sheath flow 12 or the waste liquid 32 to the current 46 can be avoided, the sensitivity of the sensor is improved and noises brought from the back sheath flow 12 or the waste liquid 32 are isolated.

Further, the embodiment fulfills the function that the back sheath flow 12 may flows from the outside of the flow cell to the inside of the flow cell during the counting process. For this purpose, the liquid level of the back sheath liquid isolating chamber 10 is raised to produce a level difference 11. Even if no high velocity liquid passes through the aperture 14 and thus no negative pressure is formed in the above area 45, particle free cleaning liquid flows from outside into the back chamber 4 and then flows from the outlet pipe 13 out of the flow cell 1 only under the action of the level difference 11. In this way, the possibility that the polluted liquid in the outlet pipe 13 might turn around to the flow cell to cause pollution can be avoided.

In fact, as shown in FIGS. 5 and 6, even with the addition of the back sheath flow 12, the turnaround and back-flow phenomenon of the liquid specimen 43 will not disappear, though it has not occurred in the back chamber 4. The liquid specimen containing particles will turn around and back-flow at a certain position 47 in the outlet pipe and turn back again when encountering the back sheath flow 12 in the turn-back route, so as to flow towards the outside of the flow cell 1. The inner wall 48 of the outlet pipe thus contacts the sample liquid and is polluted by the liquid specimen. If the initial level difference between the back sheath liquid isolating chamber 10 and the flow cell 1 is too small, or even the liquid level of the back sheath liquid isolating chamber 10 is below that of the flow cell 1, it is possible that the liquid level of the back sheath liquid isolating chamber 10 will be lowered to below that of the flow cell 1 under continuous action of the negative pressure generated by the afore-mentioned area 45. In this case, the negative pressure disappears once the liquid stops flowing through the aperture 14. Since the flow cell 1 has a higher liquid level, the liquid in the flow cell will flow towards the back sheath liquid isolating chamber 10 and push the liquid in the outlet pipe 13 to back-flow into the flow cell 1. This will pollute the back chamber 4 and affect the subsequent counting performance. In this regard, the liquid in the back sheath liquid isolating chamber 10 cannot be driven only based on the afore-mentioned area 45. Therefore, in this embodiment, the back sheath liquid isolating chamber 10 should be situated at a position higher than the flow cell 1 (especially, the back chamber 4) and its internal lowest liquid level is always higher than the highest liquid level of the flow cell 1 during the counting process, so that the liquid in the back sheath liquid isolating chamber 10 still flows into the flow cell 1 and the back chamber 4 will not be polluted even if the negative pressure of the afore-mentioned area 45 disappears.

Perfusion of the back sheath liquid isolating chamber 10 is accomplished from the sheath liquid storing chamber 20 while being driven by the positive pressure source 21 through pipes 26 and 50. While in counting, the valve V1 is closed to cut off the supply pipeline 26 of the back sheath flow and cut the back sheath flow supply pipeline 26 off the back chamber 4, so as to form the isolation air 40. An isolation air column 54 is formed due to a fact that the air enters into the back sheath liquid isolating chamber 10 through the one-way valve V8 and pipelines 53 and 50. In any period except counting, liquid may be supplied to the back sheath liquid isolating chamber 10 at any time.

Moreover, as shown in FIG. 3, the back sheath liquid isolating chamber 10 and the waste liquid isolating chamber 25 can be placed within the shielding box 31, to completely eliminate the possibility that the back sheath flow 12 or the waste liquid 32 brings interferences from outside. The back chamber 4 acts as a high-potential chamber and the front chamber 3 acts as a zero-potential chamber, and so the aperture 14 becomes the only passage for current to flow between the two electrodes 15 and 16. Meanwhile, the shielding box 31 needs only one valve V5 to control the ON/OFF state of the outlet pipe 13. The valve V5 can be a pneumatic valve, for example. Therefore, no external electromagnetic signal will be brought into the shielding box 31, thus leading to a desirable electromagnetic isolation.

By using the impedance of a sheath flow, the particle analyzer based on sheath flow impedance method may apply to the detection and analysis of the number or the volume of particles, and to other applications thereof. For example, the particle analyzer based on sheath flow impedance method may be used for a blood cell analyzer to launch in-vitro diagnosis. In this case, the analyzer may detect blood cells, or those particles, which have a diameter on the same order as blood cells and can produce suspension liquid.

While detailed descriptions have been provided with reference to specific embodiments, it is obvious that the contents noted in the description and depicted in the accompanying drawings are intended to be illustrative, but not limiting, of the scope of the invention. It is apparent to those skilled in the art that various improvements and modifications may be made without departing from the basis and spirit of the invention, the scope of which is to be defined by the attached claims herein.

What is claimed is:

1. A particle analyzer based on sheath flow impedance method, comprising:
   a flow cell; and
   a counting circuit;
   the flow cell includes a front chamber and a back chamber, the front chamber includes a particle suspension liquid inlet and a front sheath liquid inlet, the back chamber includes a back sheath liquid inlet and a waste liquid outlet, an aperture being provided between the front and back chambers so as to form a fluid passage between the front and back chambers, each of the front and back chambers being connected to the counting circuit via an electrode respectively; wherein
   the particle analyzer further comprising:
   a back sheath liquid isolating chamber, whose upper end communicates with the atmosphere on one hand and is connected to a sheath liquid storing chamber through a pipeline on the other hand, and whose lower end is connected to the back chamber through a pipeline, the back sheath liquid being stored on the bottom of the back sheath liquid isolating chamber; during a non-detection period, the back sheath liquid is supplied to the back sheath liquid isolating chamber from the sheath liquid storing chamber;
   during a detection period, the liquid passage for supplying liquid to the back sheath liquid isolating chamber is cut off, the supply of the back sheath liquid from the sheath liquid storing chamber to the back sheath liquid isolating chamber is terminated, and the back sheath liquid in the back sheath liquid isolating chamber flows to the back chamber, with a result that air enters into the back sheath liquid isolating chamber via an interface on its top to form isolation air, causing air isolation of the internal fluid passage connecting the inlet and the outlet of the back sheath liquid isolating chamber; and
   during the detection period, the level of the back sheath liquid in the back sheath liquid isolating chamber is always maintained higher than the level of the back chamber.

2. The particle analyzer according to claim 1, wherein two interfaces are provided on the top of the back sheath liquid isolating chamber, one interface is connected to a one-way valve which only allows flow of liquid from the inside of the chamber to the outside of the chamber, and the other interface is connected to a pipeline having two branches, one being connected to a sheath liquid supply source, and the other one being connected to another one-way valve which only allows flow of liquid from the outside of the chamber to the inside of the chamber and is located at the uppermost position for all fluid passages.

3. The particle analyzer according to claim 1, wherein the back sheath liquid isolating chamber is located at a position higher than the back chamber.

4. The particle analyzer according to claim 1, further comprising:
a waste liquid isolating chamber, which is located at a downstream position of the waste liquid outlet of the back chamber, the top end of the waste liquid isolating chamber is connected to the waste liquid outlet and the bottom of the waste liquid isolating chamber is connected to a waste liquid chamber, the top end of the waste liquid isolating chamber also communicates with the atmosphere, causing air isolation of the internal fluid passage connecting the inlet and the outlet of the waste liquid isolating chamber.

5. The particle analyzer according to claim 4, wherein the waste liquid isolating chamber is located at a position lower than the back chamber, and the height of the pipeline connecting the waste liquid outlet and the waste liquid isolating chamber is lower than the highest liquid level of the back chamber.

6. The particle analyzer according to claim 4, further comprising:
a flow-limiting pipe serially connected within the pipeline between the back sheath liquid isolating chamber and the back chamber, so as to limit the velocity of the back sheath liquid flowing from the back sheath liquid isolating chamber to the back chamber and ensure that the amount of the liquid ultimately flowing from the waste liquid outlet to the waste liquid isolating chamber can only form discontinuous liquid drops, instead of continuous fluid jet, so as to form air isolation between the liquid on the bottom and that on the top of the waste liquid isolating chamber.

7. The particle analyzer according to claim 4, wherein a waste liquid buffering chamber is provided at an upstream position of the waste liquid isolating chamber, so that a larger amount of waste liquid generated during the counting operation is temporarily stored in the waste liquid buffering chamber and then be discharged into the waste liquid isolating chamber.

8. The particle analyzer according to claim 7, wherein the bottom of the waste liquid buffering chamber is connected with the top of the waste liquid isolating chamber via a pipeline, the inner diameter of which is limited, so that the waste liquid is gradually discharged from the waste liquid buffering chamber into the waste liquid isolating chamber in form of liquid drops.

9. The particle analyzer according to claim 7, wherein the bottom of the waste liquid buffering chamber is connected with the top of the waste liquid isolating chamber via a pipeline, on which a valve is provided, so that the waste liquid is discharged from the waste liquid buffering chamber into the waste liquid isolating chamber under the control of the valve.

10. The particle analyzer according to claim 4, further comprising:
a grounded metal shielding box, within which the flow cell, the back sheath liquid isolating chamber and the waste liquid isolating chamber are placed.

11. The particle analyzer according to claim 10, wherein besides that the back sheath liquid and the waste liquid are isolated by the back sheath liquid isolating chamber and the waste liquid isolating chamber respectively and the pipeline communicated with the atmosphere is air blocked, all the liquid in the pipeline connected to the flow cell, the pipeline supplying liquid to the back sheath liquid isolating chamber and the pipeline leading from the waste liquid isolating chamber to the waste liquid chamber is connected to the shielding box.

12. The particle analyzer according to claim 1, wherein all the liquid in the front chamber and its two inlets is connected to a zero-potential electrode, and the back chamber is connected to a high-potential electrode, the current is unable to return to the zero-potential electrode through other passages other than the aperture, thus making the aperture to be the only passage from the high-potential electrode to the zero-potential electrode, the zero-potential electrode and the high-potential electrode are connected to the counting circuit, respectively.

13. The particle analyzer according to claim 1, wherein the front sheath liquid inlet is connected via a pipeline to a sheath liquid storing chamber, which is connected with a positive pressure source.

14. The particle analyzer according to claim 1, wherein the particle suspension liquid is introduced into the front chamber through a specimen tube and the waste liquid is discharged from the back chamber through an outlet pipe.

15. The particle analyzer according to claim 14, wherein one end of the specimen tube outside the front chamber acts as the particle suspension liquid inlet, and one end of the outlet pipe outside the back chamber acts as the waste liquid outlet.

16. The particle analyzer according to claim 1, wherein the sheath liquid storing chamber stores particle free liquid for supply.

17. The particle analyzer according to claim 1, wherein the front sheath liquid and the back sheath liquid are conductive and contain no particle, and thus forming a front sheath flow and a back sheath flow in the front chamber and the back chamber respectively during the detection period, and the particle suspension liquid containing particles to be detected forms a liquid specimen passing through the aperture.

18. The particle analyzer according to claim 1, wherein the front chamber, the back chamber and the aperture are all made of insulating materials.

19. The particle analyzer according to claim 1, wherein the aperture is provided on a cylindrical, artificial ruby sheet, and its inner diameter and depth are both less than 100 microns.

20. The particle analyzer according to claim 1, wherein during the detection period, the back sheath liquid in the back sheath liquid isolating chamber flows into the back chamber automatically and continuously due to the liquid level difference between the liquid in the back sheath liquid isolating chamber and the liquid in the back chamber, or due to a combination of said liquid level difference and the interior negative pressure of the back chamber.

* * * * *